United States Patent
McNeal et al.

(10) Patent No.: US 9,642,749 B2
(45) Date of Patent: May 9, 2017

(54) GOGGLE WITH ADJUSTABLE NOSE AREA

(71) Applicant: Smith Optics, Inc., Ketchum, ID (US)

(72) Inventors: Joseph R. McNeal, Hailey, ID (US); George T. Giroux, Hailey, ID (US)

(73) Assignee: Smith Optics, Inc., Portland, OR (US)

( * ) Notice: Subject to any disclaimer, the term of this patent is extended or adjusted under 35 U.S.C. 154(b) by 513 days.

(21) Appl. No.: 13/662,257

(22) Filed: Oct. 26, 2012

(65) Prior Publication Data

US 2014/0115761 A1     May 1, 2014

(51) Int. Cl.
*A61F 9/02*     (2006.01)
*G02C 5/12*     (2006.01)

(52) U.S. Cl.
CPC .............. *A61F 9/026* (2013.01); *G02C 5/122* (2013.01)

(58) Field of Classification Search
CPC .......... G02C 5/12; G02C 5/126; G02C 5/122; G02C 5/04; A44C 5/0092; Y10T 24/1449; Y10T 24/142; A61F 9/025; A61F 9/026; A61F 9/02; A63B 2033/004; A63B 2033/002
USPC ........... 2/426, 438, 446, 443, 439, 445, 425; 351/76, 88, 71, 137, 87; 24/68 J, 71 CT, 24/280, 131 R, 115 H
See application file for complete search history.

(56) References Cited

U.S. PATENT DOCUMENTS

| | | | |
|---|---|---|---|
| 4,556,300 A * | 12/1985 | Dietrich | G02C 5/12 351/136 |
| 4,787,730 A * | 11/1988 | Bristol | 351/138 |
| 5,884,339 A * | 3/1999 | Fukasawa | 2/446 |
| 6,106,117 A * | 8/2000 | Huang Lin | G02C 5/122 351/136 |
| 6,582,074 B1 * | 6/2003 | Chen | 351/136 |
| 7,484,843 B1 * | 2/2009 | Lin | G02C 5/126 351/136 |
| 7,971,268 B2 * | 7/2011 | Reyes et al. | 2/15 |
| 8,366,266 B2 | 2/2013 | Pulito et al. | |

(Continued)

FOREIGN PATENT DOCUMENTS

| | | | | |
|---|---|---|---|---|
| CH | WO 2011082718 A1 * | 7/2011 | | A61F 9/025 |
| IT | WO 2013079990 A1 * | 6/2013 | | A61F 9/026 |
| WO | WO2011082718 | * | 7/2011 | |

OTHER PUBLICATIONS

Examiner's Report dated Apr. 30, 2015 received for Canadian Appln No. 2,831,450.

(Continued)

*Primary Examiner* — Anna Kinsaul
*Assistant Examiner* — Jillian K Pierorazio
(74) *Attorney, Agent, or Firm* — Dorsey & Whitney LLP (57) ABSTRACT

Goggles, goggle frames, and methods for adjusting a fit of a goggle frame are disclosed. In an example goggle, the goggle includes a frame and a lens. The frame includes a lens receiving portion and a face contact portion. The face contact portion includes a nose recess including an adjustable member for changing a contour of the face contact portion. The lens is configured to be mounted to the lens receiving portion. In an example goggle frame, the goggle frame includes a lens opening for mounting a lens thereto and a nose recess portion including a fit adjustment member. The fit adjustment member is configured to be deformed from an undeformed shape to a deformed shape and to retain the deformed shape.

12 Claims, 8 Drawing Sheets

(56) References Cited

U.S. PATENT DOCUMENTS

| | | | | |
|---|---|---|---|---|
| 2003/0106139 A1* | 6/2003 | Lee | ...................... | A63B 33/002 2/426 |
| 2004/0088779 A1* | 5/2004 | Kita | .................................. | 2/443 |
| 2004/0158916 A1* | 8/2004 | Sung | .................... | A63B 33/002 2/426 |
| 2005/0052614 A1* | 3/2005 | Negishi | .................. | G02C 5/124 351/137 |
| 2005/0253999 A1* | 11/2005 | Lerner et al. | .................... | 351/92 |
| 2010/0186153 A1* | 7/2010 | Reyes | ...................... | A61F 9/029 2/427 |
| 2010/0220283 A1* | 9/2010 | Pulito | .................... | G02C 11/08 351/62 |
| 2012/0206690 A1* | 8/2012 | Chen | ...................... | G02C 5/126 351/137 |

OTHER PUBLICATIONS

Examiner's Report dated Feb. 8, 2016 received for Canadian Appln. No. 2,831,450.

* cited by examiner

FIG.1

(PRIOR ART)

GOGGLE WITH ADJUSTABLE NOSE AREA

TECHNICAL FIELD

This present disclosure generally relates to goggles, and more particularly, to goggles with an adjustable nose area.

BACKGROUND

Figure 1:
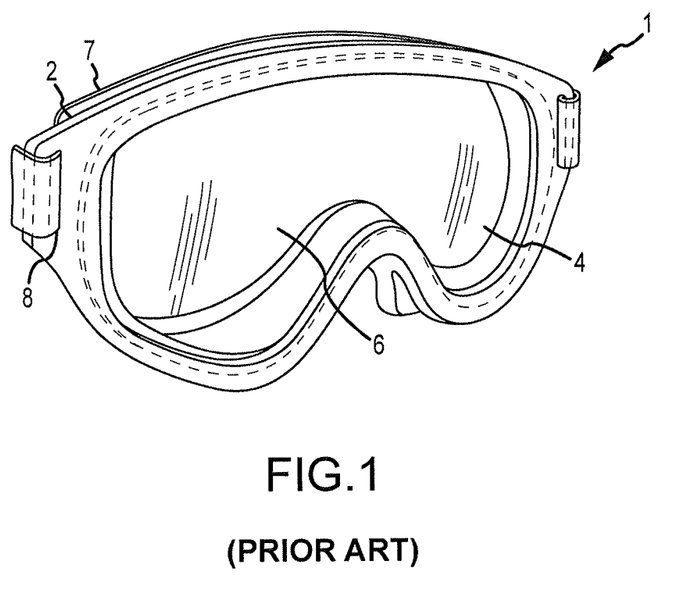
FIG. 1 is an example of a conventional goggle.

Goggles are widely used in various applications, for example when participating in sports, such as skiing and snowboarding, and when working with hazardous substances or in hazardous conditions. Goggles, for example goggle 1 as shown in FIG. 1, typically include a frame 2 and a lens 4 mounted within the frame. The frame 2 may have a generally oval shape and may include an opening 6 having a shape corresponding to the lens 4 for mounting the lens 4 thereto. The goggle 1 may be secured against the face of the wearer, for example using a strap 8. The back portion 7 of the frame 2 may be made of a soft material so that the frame 2 may generally conform to the face of the wearer. While certain portions of the frame 2, such as the back portion 7, may be constructed from flexible materials in order to achieve this goal, goggles known in the art may still fail to provide a sufficiently conforming fit as may be desired.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

Figure 2:
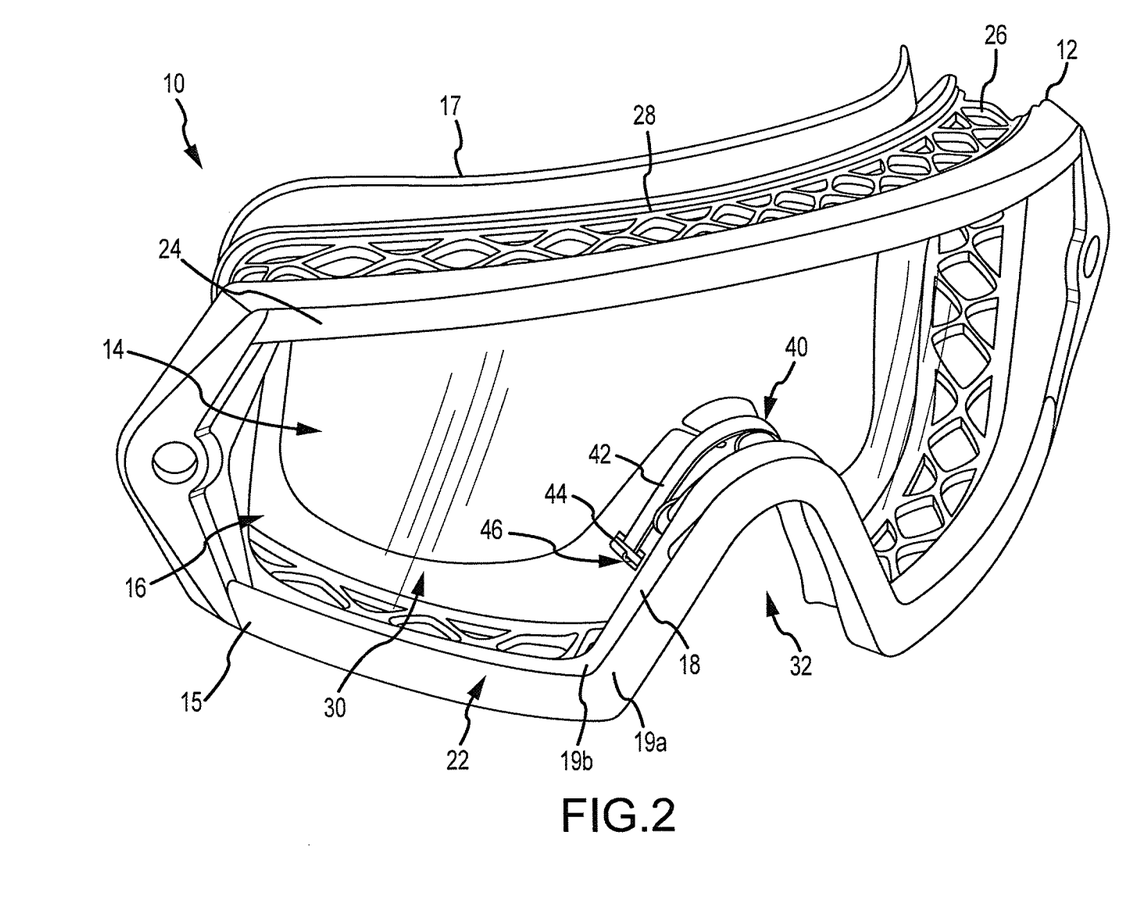
FIG. 2 is an example of a goggle according to the present disclosure.

FIG. 2 shows a goggle 10, which includes a frame 12 and a lens 14. The frame 12 may be implemented as a peripheral member with a generally oval shape. The frame 12 may include a lens receiving portion or rim 15 and a face contact portion 17. The lens receiving portion 15 may include an opening 16 for receiving and mounting the lens 14 thereto. The lens receiving portion 15 may further include a groove 18 in which an outer peripheral edge of the lens 14 may be received. The groove 18 may be defined between a front wall 19a and rear wall 19b for maintaining the lens 14 securely within the groove 18. In some examples, the groove 18 may extend along the entire circumference of the opening 16. In certain examples, the groove 18 may extend along only portions of the opening 16, for example along a bottom portion 22. The lens 14 may be fixedly or removably attached to the frame 12, for example using one or more fasteners or pivoting clips (not shown), which may be arranged along a top portion 24 of the rim 15, for example. The lens 14, which may be flat or curved, may be implemented according to any known or later developed techniques, for example, for forming single pane and double-pane lens structures. The goggle 10 may optionally include a strap (not shown) for maintaining the goggle 10 against the wearer's face. The strap may be removably or fixedly attached to the frame 12 and may be made of any suitable material, for example, an elastic material. In this manner, when placed against the wearer's face, the frame 12 and lens 14 attached thereto may define an enclosed space between the wearer's face and the interior portion of the goggle 10. Furthermore, one or more vents or other apertures 26 may be provided in the frame 12, for example to permit air to enter and exit the space between the lens 14 and the wearer's face.

The lens receiving portion 15 may be made of any of a variety of resilient polymer materials, such as a high durometer plastic material. In certain examples, the lens receiving portion 15 may be stiffer than other portions of the frame 12, for example for maintaining a flatness or a curvature of the lens 14 when the frame is secured against the face of the wearer. In other examples, the lens receiving portion 15 may be substantially as flexible as other portions of the frame 12 to allow the frame, including the lens receiving portion 15, to bend and tension against the wearer's face. The face contact portion 17 may be formed using a compliant material, for example a soft polymeric material. In certain examples, the face contact portion 17 may be softer and/or more flexible than the lens receiving portion 15 in order to cushion the frame 12 against the face of the wearer and/or provide a comfortable and conforming fit with the face of the wearer.

The lens receiving portion 15 and the face contact portion 17 may be connected using a shroud or web 28, which may be sized and/or shaped to maintain the lens 14 in a desired spaced-apart position relative to the wearer's face. That is, when the goggle 10 is positioned over the wearer's face, the goggle 10 defines a cavity 30 immediately in front of the wearer's eyes (e.g., between the wearer's face and interior surfaces of the goggle 10). The web 28, which may be made of the same or similar compliant material as the material used for the face contact portion 17, may be configured to have a desired stiffness, for example to maintain the lens 14 in a desired spaced-apart position. The web 28 and/or face contact portion 17 may be made of a variety of flexible materials including, for example elastic synthetic resins, foam (e.g., polyurethane foam), rubber, sponge-type materials, or the like. In some examples, the web 28 may comprise a porous (e.g. air permeable) material or may include one or more apertures or openings 26 extending through the thickness of the web 28. The porosity and/or configuration of the openings 26 may be selected to provide the venting functionality previously described and/or obtain a desired flexibility for achieving a conforming fit.

The frame 12 may include a nose recess portion 32. The nose recess portion 32 of the frame 12 may define a recess for accommodating the nose of the wearer. It is generally desirable that goggles, whether being used for sports or for eye protection from hazards, are designed to fit snugly over the face of the wearer. To achieve a conforming fit, the frame 12 may be made of materials capable of deforming in order to conform to the face of the wearer, for example, foam or rubber. Furthermore, in order to fit faces of various sizes and shapes (e.g., child, adult, female or male, etc.), goggles may also be available in several corresponding sizes.

However, while several different sizes of goggles and/or goggle frames may be provided for fitting faces of various sizes and shapes, certain facial features may still vary greatly even among individuals having approximately similarly sized faces. For example, some people may have a bridge and nose that are smaller or generally less pronounced than other people having comparable sized faces. Additionally, some people may have wider noses than others as well. As such, further granularity of sizing may be desirable but may be impractical from a commercial standpoint. To offer a truly customized fit, a custom sized goggle frame may be designed and built to fit the precise contours of the particular individual's face, however, such customization may be cost prohibitive for most consumers. Accordingly, an inexpensive method for achieving a more customized fit than otherwise possible with currently available goggles may be desired.

Embodiments of the present invention provide for goggles and goggle frames with adjustable portions of the frame. According to some examples, a goggle frame may have an adjustable nose area, as will be further described. While specific examples directed to goggles with adjustable nose areas are described, the inventive concepts herein may be equally applicable to adjusting any other portion of the frame. For example, the top portion 24 of the frame may be adjustable to offer an improved fit for individuals who may have more pronounced brows. Side portions or sections of the bottom portion 22, other than the nose area, may also be adjusted according to the present examples, for example, to provide a more conforming fit for individuals with sunken temples or pronounced cheek bones. Accordingly, adjustable members as described herein, or appreciated in light of this disclosure, may be implemented to obtain goggles with improved fit in virtually any area of the frame, including the nose area.

FIG. 2 depicts one example of a goggle with an adjustable portion of the frame. In the example in FIG. 2, the nose recess portion 32 of the goggle frame 12 may be configured to be adjusted. For example, the nose recess portion 32 may include a fit adjustment member 40 (interchangeably referred to herein as an adjustable member). In the example in FIG. 2, the fit adjustment member 40 is implemented as a metal strip 42 having end portions 46. However, other form factors and/or materials may be used for the fit adjustment member 40 such that the fit adjustment member 40 may be operable to vary the contour of the contact portion 17 and/or nose recess portion of the frame 12. In some examples, the fit adjustment member 40 may be removably mounted to the frame 12, as in the example shown in FIG. 2. In this regard, the frame 12 may include attachment portions 44 disposed at opposite sides of the nose recess portion 32. The attachment portions 44 may be configured such that end portions 46 of the fit adjustment member 40 may be provided therethrough, received therein, engaged therewith, or otherwise secured to the frame. In the example in FIG. 2, the end portions 46 may be shaped as hooks in order to allow the metal strip 42 to engage with the attachment portions 44, which in this example are implemented as loops.

Figures 3A, 3B:
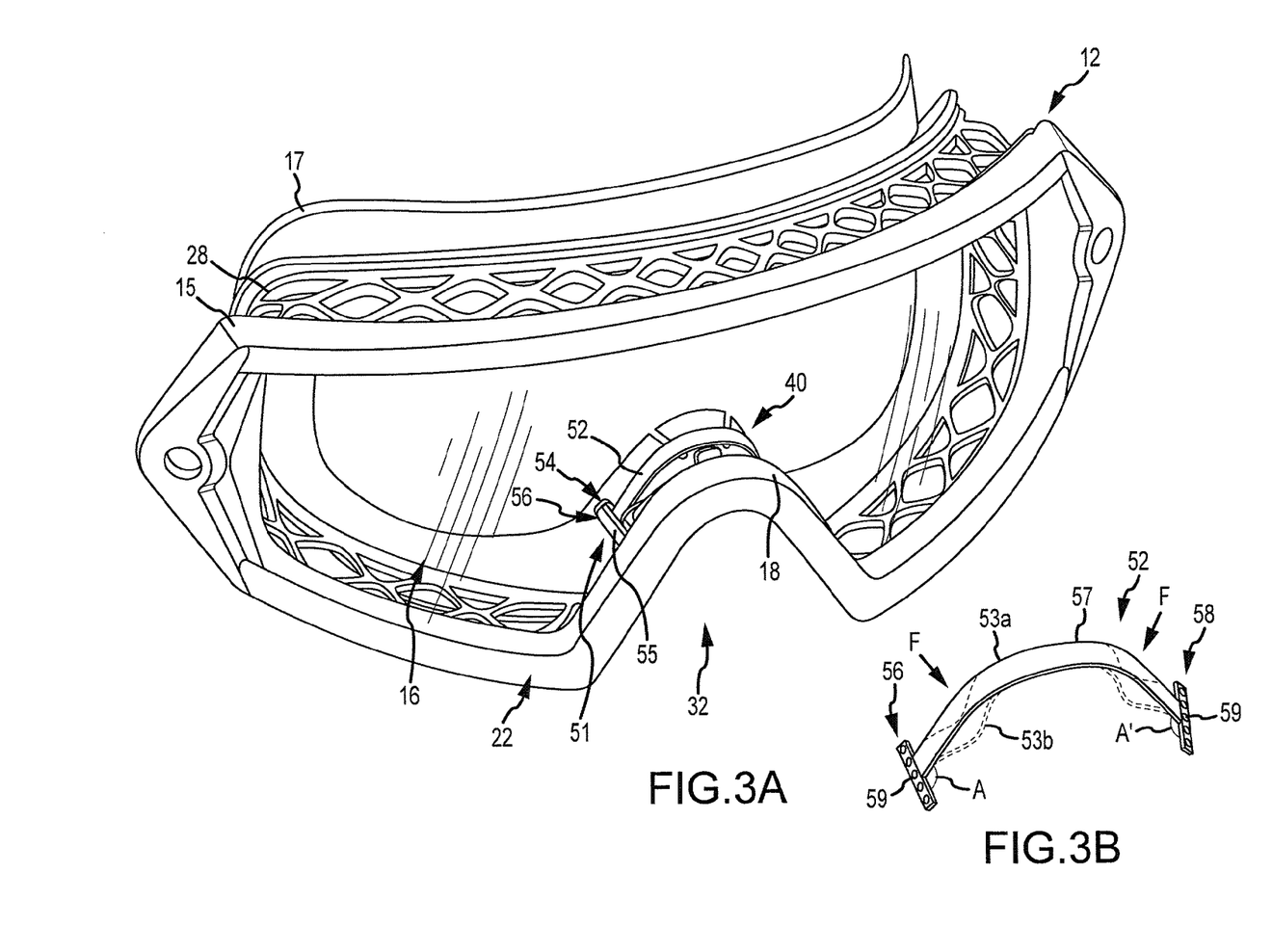
FIG. 3A is another example of a goggle according to the present disclosure.
FIG. 3B is a diagram of an adjustable member according to the present disclosure.

FIG. 3A shows another example of a goggle according to the present disclosure. The goggle includes a goggle frame 12 with a fit adjustment member 40 according to the present disclosure. The goggle frame 12 in the example in FIG. 3A may include some or all of the features of the goggle frame 12 in FIG. 2, for example a lens receiving portion 15, a face contact portion 17, and a web 28 disposed therebetween. As previously described, the lens receiving portion may include an opening 16 with a groove 18 for receiving a lens therein. For brevity, the arrangement and functionality of certain similar features of the goggle frame 12 previously described will not be repeated, and the examples described herein may be practiced using various combinations of the features described and as will be appreciated by those skilled in the art.

In the example in FIG. 3A, the adjustable member 40 may be configured as a metal strip 52 similar to the metal strip 42 (FIG. 2) but which may differ from metal strip 42 in the attachment of the metal strip 52 to the frame 12. In the example of FIG. 3A, the metal strip 52 may be coupled to the frame via the attachment portions 54, which may be molded over end portions 56, 58 of metal strip 52 so as to enclose the end portions, as will be further described.

As shown in more detail in FIG. 3B, the metal strip 52 may be generally I-shaped and may be originally provided in first configuration 53*a*. The metal strip 52 may be operable to be deformed to a second configuration 53*b*, for example, by squeezing sides of the metal strip (e.g., as shown by application of opposing forces F). The metal strip 52 then retains the second configuration 53*b*. The metal strip 52 may have end portions 56, 58 which may be wider than an intermediate portion 57, thereby providing a larger contact area for attaching the metal strip 52 to sides of the nose recess portion (e.g., at the attachment portions 54). The end portions 56, 58 may be symmetric about the longitudinal axis of the metal strip 52, or they may be longer in one direction. In some examples, the end portions 56, 58 may be angled relative to the intermediate portion 57 to define an angle A, A' other than 90 degrees. By angling the end portions 56, 58 relative to the intermediate portion, a smaller area 51 between the front portion 22 and the edge of the face contact portion 17 may suffice for coupling the adjustable member 40 to the frame 12. In this regard, such an angled configuration (e.g., an angle A less than 90 degrees) may be suitable for wearers with shallower and/or wider noses.

The metal strip 52 in this example is fixedly (e.g., permanently) attached to the frame 12, which can be achieved by molding the end portions 56, 58 within the attachment portions 54, implemented in this example as sleeves or pockets 55, for example. The end portions 56, 58 of the metal strip 52 may include one or more holes 59 or other surface features for improved grip between the metal strip and the attachment portions 54. For example, during the molding process, the plastic material molded over the end portions 56, 58 may flow through the holes 59 thereby engaging with the end portions 56, 58 and forming a more secure attachment than would be achieved in the absence of holes 59. In some examples, the metal strip 52 may instead be configured to be removably attached to the nose recess portion 32. For example, slits may be provided along one or more edges and through a portion of the thickness of the attachment portions 54 such that the end portions 56, 58 may be inserted into engagement within the pockets 55. The end portions 56, 58 may be maintained in engagement within the pockets 55 by friction, for example. Nubs or other surface features may be provided on interior surfaces of the pockets 55 which may cooperate with the holes 59 or other surface features of the metal strip 52.

Figure 4:
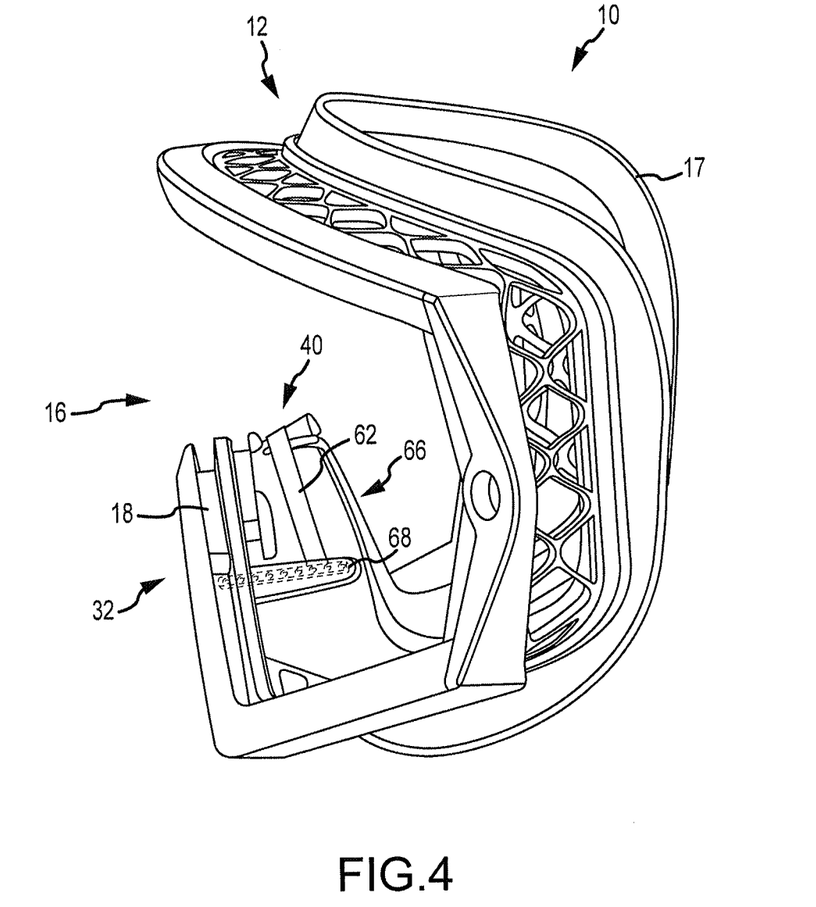
FIG. 4 is a side view of an example of a goggle frame according to the present disclosure.

FIG. 4 shows another example of a goggle frame 12 and fit adjustment member according to the present invention. The fit adjustment member 40 is implemented as a strip 62 in the example of FIG. 4. End portions 66, 68 of the strip 62 may extend below or through a bottom portion of the groove 18. By providing the end portions 66, 68 of the strip 62 under the lens (not shown in this example), the strip 62 may be better supported in place (e.g., maintained against the wearer's nose by a slight downward force applied by the lens). As previously described with reference to FIG. 3A, the fit adjustment member 40 in the present example may also be removably or fixedly mounted to the frame according to any of the examples herein. As will be appreciated, the specific examples described herein are provided for illustration and fit adjustment members may be implemented according to many other configurations and form factors without departing from the scope of the present invention.

Figure 5A:
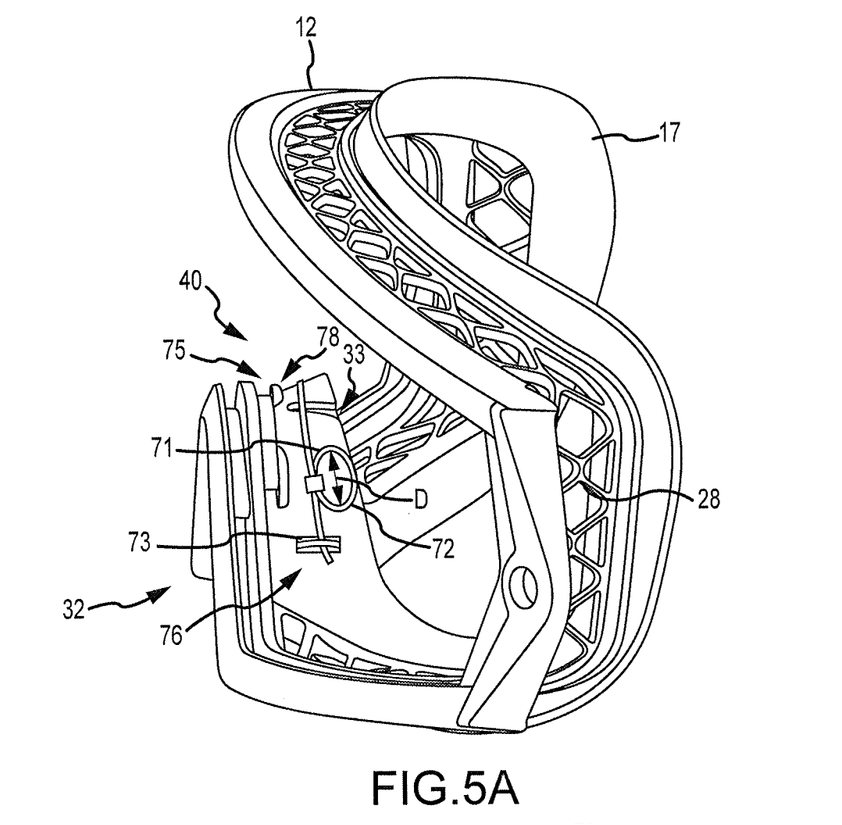
FIG. 5A is a side view of an example of a goggle frame with an adjustment member implemented using a wire.
Figure 5B:
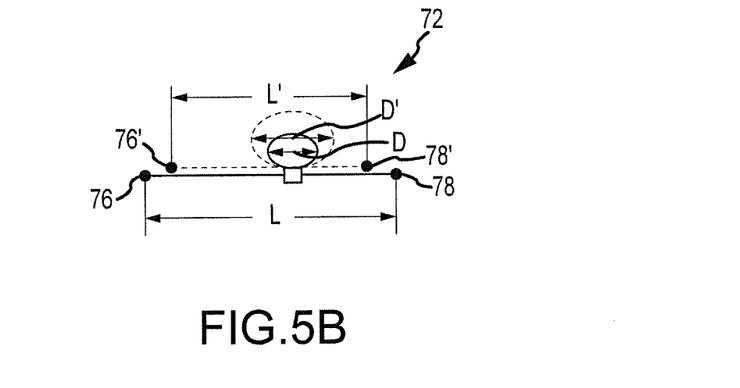
FIG. 5B is an illustration of a fit adjustment member according to the example in FIG. 5A.
Figure 6:
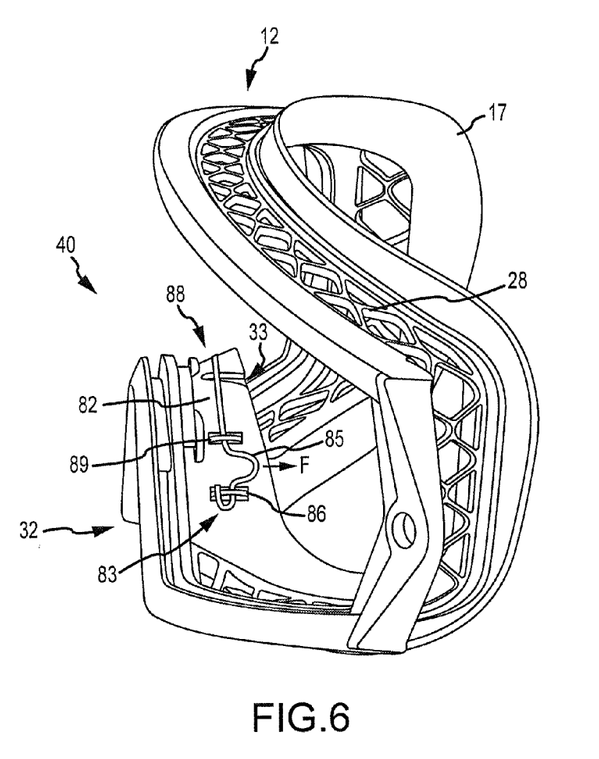
FIG. 6 is a side view of another example of a goggle frame with an adjustment member implemented using a wire.
Figure 7:
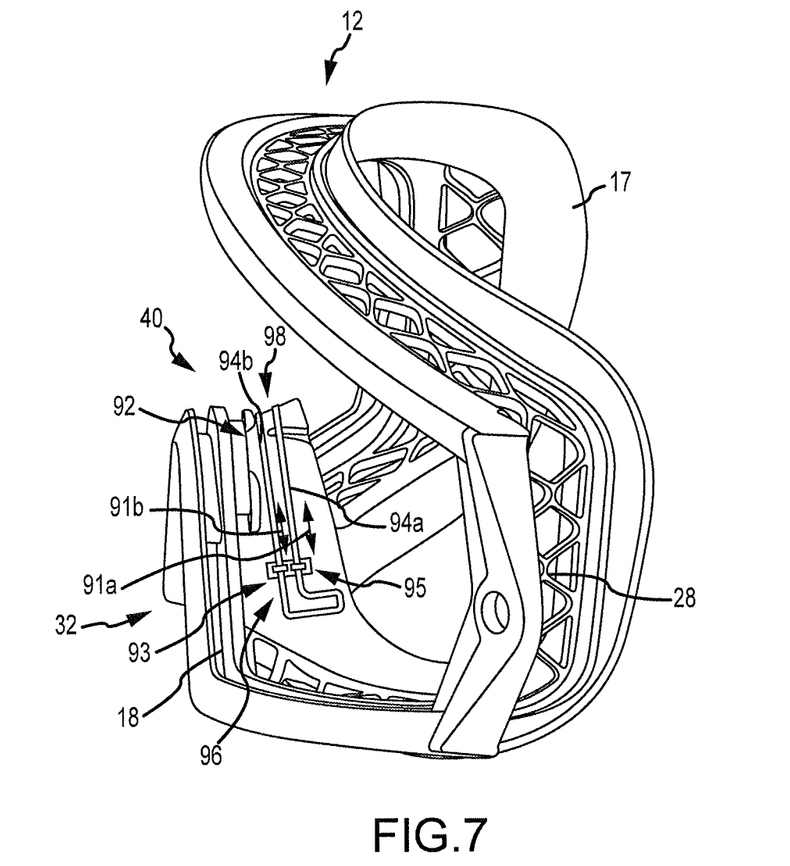
FIG. 7 is a side view of yet another example of a goggle frame with an adjustment member implemented using a plurality of a wires.

For example, the fit adjustment member 40 may be implemented as a wire (as shown in FIGS. 5A, 5B, and 6), or a plurality of wires or strands (as shown in FIG. 7). Combinations of strips and wires may also be used. In other examples, the fit adjustment member 40 may be made of a resilient polymer instead of metal, which may be configured to allow the polymer member to deform and retain its deformed shape. In yet other examples, the fit adjustment member 40 may be implemented using a shape memory alloy which may be configured to contract upon the application of a small voltage.

The fit adjustment member 40 may be embedded or integrated in the frame. In examples where the fit adjustment member is a separate component (e.g. metal strip 42, 52), the fit adjustment member 40 may be enclosed or embedded within the material frame, for example by over molding, rather than being "attached" to the frame and/or exposed/visible to the wearer. In some instances, the fit adjustment member may be integrated with the nose recess portion 32. In this regard, the nose area of the goggle may be adjustable by virtue of being formed from a material capable of retaining a deformed shape. For example, the nose recess portion 32 (also referred to as nosepiece or nose bridge) made from a plurality of layers of molded plastic, some or all of which may have different stiffness or other physical characteristics. For example, the nosepiece may include a lay-up of different plies of polymeric material, one or more of the which may be shape memory materials. In some examples, a shape memory foam may be used in conjunction with other examples of fit adjustment member described herein.

Referring now to the examples in FIGS. 5-7, several examples of fit adjustment members using one or more wires will be described. The fit adjustment member 40 in FIG. 5A is implemented using a single, looped wire 72. The looped wire 72 in FIG. 5A is configured such that the nose recess portion 32 may be adjusted (e.g., adjusting contour, shape, size, etc.) by enlarging the size of the loop 71, as illustrated in FIG. 5B. For example, the ends of the wire 76, 78 may be fixedly attached to the attachment portions 73, 75, defining a fixed length L of the looped wire 72. When a wearer desires to adjust the fit of the nose area, the wearer may vary the diameter D of the loop 71, for example, by increasing said diameter by the application of an outward force within the perimeter of loop 71. In this regard, increasing the diameter D may result in shortening of the effective length (shown in FIG. 5B as L') between the ends 76, 78 thus decreasing the distance between the attachment portions 73, 75. This may cause the attachment portions 73 and 75 disposed on opposite sides of the nose recess portion 32 to be brought closer together and/or may result in compressing or squeezing the soft material disposed at the nose recess portion 32. Slits 33 may be formed in the soft material to facilitate the adjustment of the fit as described.

FIG. 6 shows another example of a goggle frame 12 with an adjustable nose area. Similar to the example in FIG. 5A, the fit adjustment member (or adjustable member) 40 in FIG. 6 is implemented using a wire 82. While a single wire 82 is depicted for illustrative purposes, it will be understood that any number of wires, bundled, stranded or braided, may instead be used. End portions 83 of the wire 82 may be fixedly attached to attachment portions 86, 88 disposed on opposite sides of the nose recess portion. One or more additional attachment portions 89 (e.g., loops, hooks, or the like) may be used at intermediate portions along the length of the wire 82 to allow for the distance between the attachment portions 86 and 88 to be varied. The wire 82 may be slidably coupled with the loop 89 (e.g., wire 82 may be passed through the loop 89). In use, the wearer may apply a force F in the direction indicated to increase the transverse dimension of the pull member 85, which may cause the effective distance between the end portions 83 of the wire to decrease. In a similar manner to the example in FIG. 5A, this may result in the attachment portions 86, 88 being brought closer together. In some embodiments, the wire 82 may be sufficiently malleable to be deflected by the wearer with ease and yet sufficiently stiff to retain the deformed shape upon release of the pulling force F. In other examples, the loop 89 may provide sufficient friction to prevent the wire 82 from freely sliding through the attachment portion (e.g., loop) 89. As will be understood, the fit adjustment member 40 may be implemented to include any combination of the features described without departing from the scope of the present disclosure.

FIG. 7 shows yet another example of a goggle frame according to the present disclosure. In this example, the fit adjustment member 40 includes a plurality of wires 92. The individual wires 94a, 94b may or may not be parallel to each other. Each of the wires may be slidably engaged with attachment portions 96, 98 of the nose area, and each of the wires 94a, 94b may be individually movable within openings 93, 95 of the attachment portions. As such, each of the wires may be individually movable along directions 91a, 91b to allow for adjustment of the nose area along a plurality of axes. For example, the first or inner strand 94a may be adjustable along the direction 91a to a first length and the second or outer strand 94b may be adjustable along the direction 91b to a second length, which may be different than the first length. By adjusting the different wires to different lengths certain portions of the nose area may be squeezed more than other portions thereby facilitating adjustment in the three dimensional space defined by nose recess portion 32 of the frame.

Figure 8:
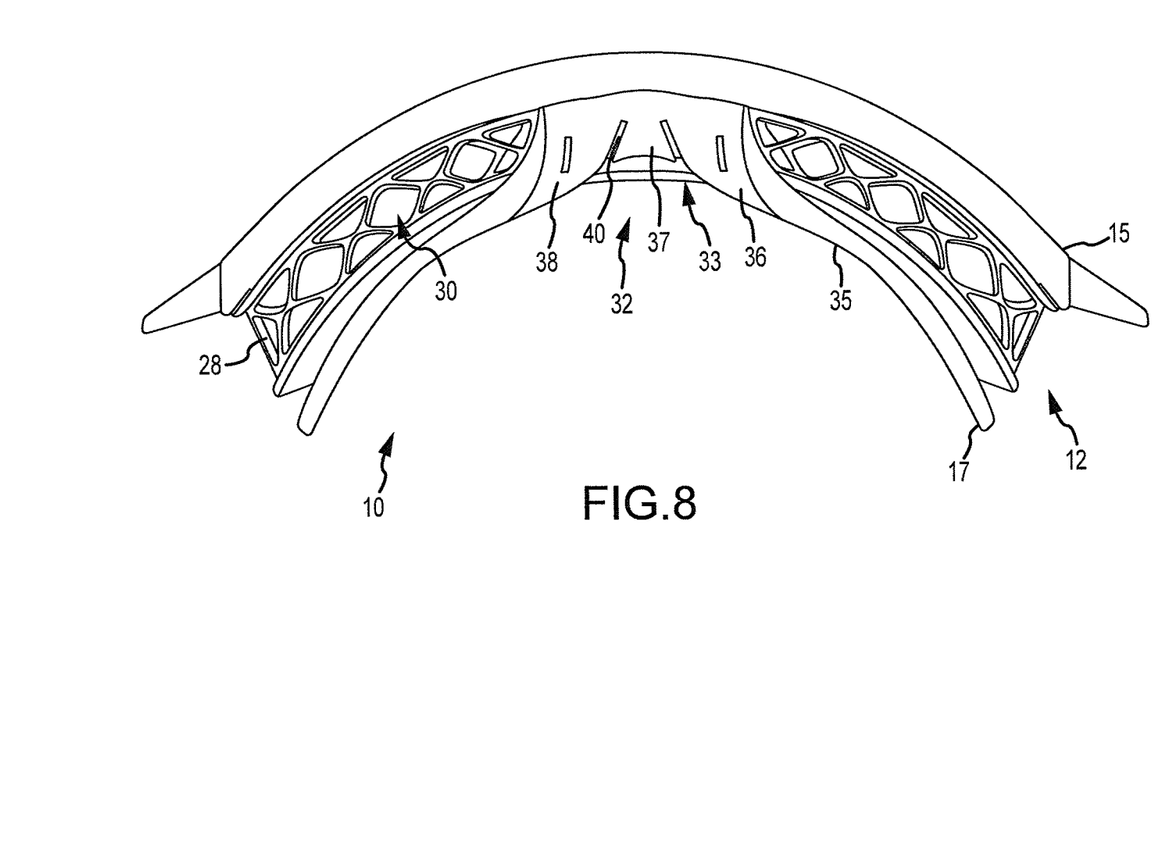
FIG. 8 is a bottom view of a goggle frame according to the present disclosure.

FIG. 8 shows a bottom view of a goggle frame according to one example. As previously described and as depicted more clearly in FIG. 8, in some examples, the nose recess portion 32 may include one or more through-thickness slits or notches 33 at the nose area (e.g., nose recess portion 32). In other examples, instead or in combination with slits, the material of the nose area may be weakened, for example by thinning or perforating the material. Such weakening of the material may facilitate the expansion and/compression of the nose area when the fit of the nose area is being adjusted by the wearer. The one or more notches 33 may extend from a perimeter 35 of the face contact portion 17 inwardly towards the interior of the cavity 30 thereby defining a plurality of sections 36-38. Three sections, first side section 36, second side section 38, and top section 37 are shown in this example, but it will be understood that any number of sections may be used. For example, the nose area may be split into two side sections only, or it may be split into any odd (for example, five) or any even number of sections. In this regard, the nose recess portion 32 of the frame 12 may be configured to expand slightly when placed over the nose of the wearer. The first and second side sections 36, 38 may conform to sides of the wearer's nose, while a top or central portion 37 may displace slightly upwards from the two sides 36 and 28 to conform generally to a top portion of the wearer's nose. However, as described herein, even with segmenting the nose area into a plurality of sections, a closely conforming fit may still be difficult to obtain with regards to portions of the wearer's nose which are concave. In this regard, fit adjustment members 40 as described herein may be utilized to improve the conformance of the goggle over such difficult to fit areas of the wearer's face.

Goggle frames and goggles with an adjustable portions along the perimeter of the frame may be implemented according to the examples described herein. For example, goggles with adjustable nose area (also referred to herein as nose recess portion) are described. A goggle frame according to one example of the present disclosure may include a lens opening for mounting a lens thereto, and a nose recess portion including a fit adjustment member, which may be configured to deform to a deformed shape upon the application of a force thereto and to retain the deformed shape upon removal of the applied force.

The fit adjustment member may be a strip or other elongate member, which may be made of metal or plastic material. The fit adjustment member may be fixedly or removably attached to the frame. In certain examples, the fit adjustment member may be attached to the frame only along certain portions of the fit adjustment member, for example along its end portions. In such examples, an intermediate portion defined between the end portions of the fit adjustment member may be free to move relative to the nose recess portion. In some examples, the fit adjustment member may be implemented as a generally I-shaped member. That is, the fit adjustment member may include a first and second end portions disposed at first and second ends of an intermediate portion of the fit adjustment member, and the first and second end portions may have a width greater than a width of the intermediate portion. In this regard, such an I-shape configuration of the fit adjustment portion may provide better control for adjusting the fit of the nose area. For example, the end portions of the I-shaped member may extend under the lens and be supported or forced downward by the generally rigid lens. The application of the downward force may allow for an improved fit to be achieved between the nose recess portion of the frame and the wearer's nose.

In some examples, end portions of the fit adjustment member may be attached to the frame, for example at opposite sides of the nose recess portion. The end portions may be molded with the frame so as to form part of an integral structure. In other examples, the end portions may be secured to the frame using a plurality of attachment portions, for example loops, hooks, sleeves or pockets, or the like. In some examples, the end portions of the fit adjustment member may extend upwards (e.g. generally orthogonally) to the longitudinal surface of the fit adjustment member, or they may be shaped to define hooks for attaching the hooks through corresponding loops provided in the nose recess portion.

In some examples, the fit adjustment member may be implemented as a strand of wire or a plurality of wires, which may facilitate adjustment of the fit along multiple axes. Generally, the nose recess portion of the frame may be made of a soft material, such as foam, a sponge-type material, or the like, which may be compressible under a certain force. In other examples, the nose recess portion may include slits or cutouts, which may facilitate expanding or contracting of the contour of the nose area. The nose recess portion may also include a first attachment portion and a second attachment portion adapted for coupling the fit adjustment member thereto, the member being operable to decrease a distance between the first and second attachment portions along a longitudinal direction of the fit adjustment member. In certain examples, the fit adjustment member may be implemented as a plurality of individual elongate members, for example a plurality of generally parallel wires. The fit adjustment member of such examples may be operable to adjust the fit of the nose area along a plurality of axes and may thus provide a more customized fit in a three dimensional space.

A goggle according to some examples herein may include a frame with a lens receiving portion and a face contact portion, the face contact portion including a nose recess which may have an adjustable member for changing a contour of the face contact portion. The goggle may also include a lens configured to be mounted, fixedly or removably, to the lens receiving portion of the frame. In some examples, the adjustable member of the nose area may be accessible through the lens opening of the frame. In other examples, the adjustable member may be accessible from an exterior portion of the goggle (e.g., when the lens is attached to the lens opening). For example, a control mechanism, such as a knob, a crank, a wire, a push button, or other such devices, which may couple the adjustable member to an exterior portion of the frame, may be implemented to allow the wearer to manipulate the adjustable member from the outside of the goggle. As used in the context of this disclosure, the interior of the goggle includes those portions of the goggle which become enclosed by the face of the wearer when the goggle is provided against the face of the wearer, while exterior portions are such portions which are accessible when the goggle is against the face of the wearer.

Example method for adjusting a fit of a goggle frame may include placing the goggle frame in contact with the face of the wearer, and manipulating a fit adjustment member to change a contour of a portion of the goggle frame, the fit adjustment member being configured to retain the deformed shape. In some examples, manipulating the fit adjustment member occurs prior to installing the lens, which in such examples is removably attached to the goggle frame. In other examples, manipulation of the fit adjustment member may occur at any time, including after the installation of the lens. In such examples, the manipulating of the fit adjustment member may involve controlling the fit adjustment member from the exterior of the goggle frame using a control mechanism provided through the goggle frame.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed:

1. A goggle frame comprising:
    a lens receiving portion including top, bottom, and side portions which define a lens opening for mounting a lens thereto, wherein the top, bottom, and the side portions of the lens receiving portion are configured to extend along top, bottom and side perimeter portions of the lens;
    a face contact portion opposite the lens receiving portion and comprising top, bottom, and side portions connected to respective top, bottom and side portions of the lens receiving portion, the face contact portion comprising a nose recess portion along the bottom portion of the face contact portion;
    a web connecting at least some of the top, bottom, and side portions of the face contact portion to respective top, bottom, and side portions of the lens receiving portion; and
    a fit adjustment member coupled to the nose recess portion, wherein the nose recess portion includes a first attachment portion and a second attachment portion, wherein the fit adjustment member is operable to decrease a distance between the first and second attachment portions along a longitudinal direction of the fit adjustment member, wherein the fit adjustment member includes a pull member, and wherein an increase of a transverse dimension of the pull member causes a decrease in the distance between the first and second attachment portions along the longitudinal direction of the fit adjustment member.

2. The goggle frame of claim 1, wherein the fit adjustment member is removably mounted to the nose recess portion.

3. The goggle frame of claim 1, wherein the fit adjustment member is attached to the goggle frame along only end portions of the fit adjustment member.

4. The goggle frame of claim 1, wherein ends of the fit adjustment member extend upwards from a longitudinal surface of the fit adjustment member.

5. The goggle frame of claim 1, wherein the fit adjustment member comprises a first and second end portions disposed at first and second ends of an intermediate portion of the fit adjustment member, the first and second end portions having a width greater than a width of the intermediate portion.

6. The goggle frame of claim 5, wherein the lens opening includes a groove for receiving the lens, and wherein one or more of the first and second end portions extend through or under the groove of the lens opening.

7. The goggle frame of claim 1, wherein the fit adjustment member comprises a metal strip.

8. The goggle frame of claim 1, wherein the fit adjustment member comprises a wire.

9. The goggle frame of claim 1, wherein the nose recess portion includes a first plurality of attachment portions and a second plurality of attachment portions, the fit adjustment member being operable to decrease a distance between respective ones of the first and second pluralities of attachment portions to vary a contour of the face contact portion along two or more axes.

10. A goggle frame comprising:
    a lens receiving portion including top, bottom, and side portions which define a lens opening for mounting a lens thereto, wherein the top, bottom, and the side portions of the lens receiving portion are configured to extend along top, bottom and side perimeter portions of the lens;
    a face contact portion opposite the lens receiving portion and comprising top, bottom, and side portions connected to respective top, bottom and side portions of the lens receiving portion, the face contact portion comprising a nose recess portion along the bottom portion of the face contact portion;
    a web connecting at least some of the top, bottom, and side portions of the face contact onion to respective top, bottom, and side portions of the lens receiving; and
    a fit adjustment member coupled to the nose recess portion, wherein the nose recess portion includes a first attachment portion and a second attachment portion, wherein the fit adjustment member is operable to decrease a distance between the first and second attachment portions along a longitudinal direction of the fit adjustment member, and wherein the fit adjustment member comprises a wire that forms a loop, wherein when a diameter of the loop increases, the distance between the first and second attachment portions along a longitudinal direction of the fit adjustment member decreases.

11. The goggle frame of claim 1, wherein the fit adjustment member comprises a plurality of wires.

12. The goggle frame of claim 11, wherein the plurality of wires are parallel along the longitudinal direction of the fit adjustment member.

* * * * *